(12) United States Patent
Schmidt

(10) Patent No.: US 9,370,667 B2
(45) Date of Patent: Jun. 21, 2016

(54) DOUBLE HELIX CONDUCTOR FOR MEDICAL APPLICATIONS USING STEM CELL TECHNOLOGY

(71) Applicant: Medical Energetics, Ltd., San Diego, CA (US)

(72) Inventor: David G. Schmidt, Poway, CA (US)

(73) Assignee: Medical Energetics Ltd, Galway (IE)

( * ) Notice: Subject to any disclaimer, the term of this patent is extended or adjusted under 35 U.S.C. 154(b) by 197 days.

(21) Appl. No.: 14/247,171

(22) Filed: Apr. 7, 2014

(65) Prior Publication Data

US 2015/0283393 A1    Oct. 8, 2015

(51) Int. Cl.
| | |
|---|---|
| A61N 1/00 | (2006.01) |
| A61N 2/00 | (2006.01) |
| A61N 2/02 | (2006.01) |
| H01F 5/00 | (2006.01) |

(52) U.S. Cl.
CPC ....... A61N 2/004 (2013.01); A61N 2/02 (2013.01); H01F 5/00 (2013.01)

(58) Field of Classification Search
CPC ................................. A61N 2/02; A61N 2/008
USPC ......................................................... 600/9–15
See application file for complete search history.

(56) References Cited

U.S. PATENT DOCUMENTS

| | | |
|---|---|---|
| 1,898,661 A | 2/1933 | Hagen |
| 2,035,274 A | 3/1936 | Mougey ........................ 173/265 |
| 3,066,295 A | 11/1962 | Krause et al. ................. 343/874 |
| 3,760,812 A | 9/1973 | Timm et al. ................... 128/418 |
| 3,774,452 A | 11/1973 | Tullos et al. .................... 73/418 |
| 4,266,532 A | 5/1981 | Ryaby et al. .................. 128/1.5 |
| 4,439,702 A | 3/1984 | Belikov et al. ................. 310/80 |
| 4,489,276 A | 12/1984 | Yu ................................. 324/338 |
| 4,832,051 A | 5/1989 | Jarvik et al. .................. 128/784 |
| 5,077,934 A | 1/1992 | Liboff et al. ..................... 47/1.3 |
| 5,079,458 A | 1/1992 | Schuster ......................... 310/12 |
| 5,173,669 A | 12/1992 | Manoly ......................... 333/162 |
| 5,182,537 A | 1/1993 | Thuis |
| 5,339,061 A | 8/1994 | Reick |
| 5,359,340 A | 10/1994 | Yokota |
| 5,366,493 A | 11/1994 | Scheiner et al. .............. 607/116 |
| 5,464,456 A | 11/1995 | Kertz ............................... 47/1.3 |
| 5,654,723 A | 8/1997 | Craven et al. ................. 343/742 |
| 5,819,467 A | 10/1998 | Zucker ............................ 47/1.3 |
| 5,892,480 A | 4/1999 | Killen |
| 5,909,165 A | 6/1999 | Leupold ........................ 335/210 |
| 5,954,630 A | 9/1999 | Masaki et al. .................. 600/28 |
| 5,977,932 A | 11/1999 | Robinson |
| 6,005,462 A | 12/1999 | Myers ........................... 335/220 |
| 6,169,523 B1 | 1/2001 | Ploussios ...................... 343/895 |
| 6,239,760 B1 | 5/2001 | Van Voorhies ............... 343/742 |
| 6,300,920 B1 | 10/2001 | Pertl et al. ..................... 343/895 |
| 6,552,530 B1 | 4/2003 | Vaiser |

(Continued)

FOREIGN PATENT DOCUMENTS

| | | |
|---|---|---|
| GB | 479841 | 2/1938 |
| GB | 2480610 | 11/2011 |

(Continued)

*Primary Examiner* — John Lacyk
(74) *Attorney, Agent, or Firm* — Sheppard Mullin Richter & Hampton LLP

(57) ABSTRACT

An electrical system controlled, driven by and/or based on one or both of naturally occurring electrophysiological signals in a patient's body and/or digital audio files is used to produce electromagnetic fields to assist stem cell technology.

19 Claims, 4 Drawing Sheets

(56) References Cited

U.S. PATENT DOCUMENTS

| | | |
|---|---|---|
| 6,770,023 B2 | 8/2004 | Vaiser et al. ............... 600/13 |
| 6,921,042 B1 | 7/2005 | Goodzeit et al. ............ 242/430 |
| 6,978,179 B1 | 12/2005 | Flagg |
| 7,148,783 B2 | 12/2006 | Parsche et al. ............. 336/225 |
| 7,154,368 B2 | 12/2006 | Sweeney et al. ............ 336/229 |
| 7,375,449 B2 | 5/2008 | Butterfield ................. 310/207 |
| 8,463,407 B2 | 6/2013 | Bulkes |
| 8,652,023 B2 | 2/2014 | Schmidt ...................... 600/13 |
| 8,653,925 B2 | 2/2014 | Schmidt ...................... 336/188 |
| 8,749,333 B2 | 6/2014 | Schmidt |
| 8,919,035 B2 | 12/2014 | Schmidt |
| 8,961,384 B2 | 2/2015 | Schmidt |
| 9,030,283 B2 | 5/2015 | Schmidt |
| 2003/0158585 A1 | 8/2003 | Burnett |
| 2003/0169132 A1 | 9/2003 | Vaiser |
| 2005/0121396 A1 | 6/2005 | Kosakewich ................ 210/748 |
| 2008/0161884 A1 | 7/2008 | Chandler et al. ............ 607/50 |
| 2008/0266203 A1 | 10/2008 | Rossetto et al. ............ 345/895 |
| 2009/0206974 A1 | 8/2009 | Meinke ...................... 336/224 |
| 2009/0260849 A1 | 10/2009 | Cardas |
| 2010/0005711 A1 | 1/2010 | McNeff ...................... 47/1.4 |
| 2010/0057655 A1 | 3/2010 | Jacobson et al. ............ 706/45 |
| 2010/0113862 A1 | 5/2010 | Kotowich |
| 2010/0152811 A1 | 6/2010 | Flaherty |
| 2010/0179630 A1 | 7/2010 | Williams .................... 607/127 |
| 2012/0101366 A1 | 4/2012 | Ruohonen |
| 2012/0143285 A1 | 6/2012 | Wang |
| 2012/0223800 A1 | 9/2012 | Schmidt ...................... 336/229 |
| 2013/0192129 A1 | 8/2013 | Schmidt ...................... 471/1.3 |
| 2013/0211181 A1 | 8/2013 | Schmidt ...................... 600/13 |
| 2013/0285782 A1 | 10/2013 | Schmidt ...................... 336/73 |
| 2014/0097925 A1 | 4/2014 | Schmidt |
| 2014/0100412 A1 | 4/2014 | Schmidt |
| 2014/0218149 A1 | 8/2014 | Schmidt |
| 2014/0371514 A1 | 12/2014 | Schmidt |
| 2015/0119630 A1 | 4/2015 | Schmidt |
| 2015/0119631 A1 | 4/2015 | Schmidt |
| 2015/0119632 A1 | 4/2015 | Schmidt |
| 2015/0157871 A1 | 6/2015 | Schmidt |
| 2015/0283394 A1 | 10/2015 | Schmidt |

FOREIGN PATENT DOCUMENTS

| | | |
|---|---|---|
| WO | WO 2012/118971 | 9/2012 |
| WO | WO 2013/112810 | 8/2013 |
| WO | WO 2013/123009 | 8/2013 |

DOUBLE HELIX CONDUCTOR FOR MEDICAL APPLICATIONS USING STEM CELL TECHNOLOGY

FIELD OF THE INVENTION

The invention relates to electrical devices and/or systems configured to treat patients undergoing stem cell treatment, and, in particular, devices and systems in which a generated electromagnetic field is used to assist medical applications using stem cell technology.

BACKGROUND OF THE INVENTION

It is known that spirally wound electrical conductors exhibit certain electromagnetic properties and/or can be used to generate particular electromagnetic fields. For example, it is known that an electromagnetic coil may act as an inductor and/or part of a transformer, and has many established useful applications in electrical circuits. Applications of an electromagnetic coil may exploit the electromagnetic field that is created when, e.g., an active current source is operatively coupled to the electromagnetic coil.

It is known that stem cells have the potential to develop into many different cell types in a living organism, particularly during early life and growth. In addition, in many tissues stem cells serve a repair function.

SUMMARY

One aspect of the invention relates to a system for providing therapy to a subject undergoing stem cell treatment and/or promoting health effects in a subject undergoing stem cell treatment. As used herein, the term "stem cell treatment" may refer to any medical application using stem cell technology, including but not limited to stem cell transplantation. The system may include one or more of a field generator, one or more physical processors, one or more current sources, one or more sensors, a transducer, and/or other components.

When stem cells divide, each new cell has the potential to remain a stem cell (e.g. an unspecialized stem cell) or become another type of cell with a more specialized function, including but not limited to a muscle cell, a red blood cell, a brain cell, and/or other types of cells. Under certain conditions, stem cells may be induced to become a particular tissue-specific or organ-specific cell with special functions. Electromagnetic fields may be a contributing factor to establish certain functions.

The field generator may be configured to generate electromagnetic fields. In some embodiments, a field generator may include one or more of a support structure including two or more helically intertwined runners around which one or more conductive wires are wound, one or more sources of (alternating) current, and/or other components. The one or more conductive wires may include electrical leads, e.g. two electrical leads per conductive wire. The field generator may be configured to generate an electromagnetic field in response to one or more electric currents being induced across the electrical leads.

A conductive wire may be wound spirally around a first runner and/or a second runner. In some embodiments, a conductive wire may be wound spirally around each runner, e.g. in embodiments that include a first wire and a second wire. In some embodiments, multiple conductive wires may be wound spirally around individual runners. The leads of one or more conductive wires may be configured to be electrically coupled with one or more current sources to receive one or more currents through the conductive wires such that an electromagnetic field is created at or near the centroid that provides therapy to the subject.

As used herein, a "wire" may include a set of twisted wires (which may interchangeably be referred to as a "twisted wire"), including but not limited to a set of two twisted wires. The number of turns of a set of twisted wires per inch and/or per helical revolution of a runner may be characteristic measurements/features of the system. In some embodiments, the number of twists per inch of a twisted wire may be about 2, about 5, about 10, about 20, about 100, and/or another suitable number of twists. In some embodiments, the frequency characteristics of an alternating current and/or the corresponding generated electromagnetic field may be based on, proportional to, and/or otherwise related to the number of twists of a twisted wire. For example, a higher number of twists per inch may correspond to a higher operating frequency for the alternating current and/or the corresponding generated electromagnetic field. In some embodiments, multiple twisted wires (e.g. a first twisted wire wound around a first runner and a second twisted wire wound around a second runner) may have the same direction of twisting, and/or a different direction of twisting.

The one or more current sources may be configured to induce one or more currents across the electrical leads of one or more conductive wires, including but not limited to the electrical leads of the field generator. In some embodiments, the one or more currents may include an alternating current.

In some embodiments, the system may include one or more sensors that may be configured to generate output signals conveying electrophysiological information. The one or more sensors may be configured to generate output signals pertaining to measurements of electrophysiological information of the subject. By way of non-limiting example, electrophysiological information may include information related to one or more organs of the subject, including but not limited to heart, brain, kidney, liver, pancreas, and/or other organs of the subject. As used herein, the term "body parts" includes any organs of the subject, any cells of the subject, as well as any other parts of the body of the subject.

In some embodiments, the system may include one or more processors configured to execute computer program components. The one or more processors may include one or more physical processors. The computer program components may include one or more of an input component, a processing component, a playback component, and/or other computer program components.

The input component may be configured to obtain information, e.g. from one or more digital audio files, or, alternatively and/or simultaneously, based on sensor-generate output signals. The processing component may be configured to process the obtained information from the input component. In some embodiments, the processing component may be configured to generate a processed signal based on the obtained information form the input component. The playback component may be configured to produce sound signals based on one or more of the obtained information from the input component and/or the processed signal from the processing component. The sound signals produced by the playback component may be coupled electrically to the leads of the one or more conductive wires such that the induced current corresponds to and/or is based on the sound signals. Alternatively, and/or simultaneously, the induced current may be controlled by and/or based on the sound signals produced by the playback component.

In some embodiments, one or more frequencies of the induced (alternating) current may correspond to one or more frequencies of either the sensor-generated output signals and/or the sound signals produced by the playback component.

In some embodiments, one or more induced currents may correspond to one or more sensor-generated output signals. In some embodiments, the system may include a transducer. The transducer may be configured to convert acoustic signals to electrical signals and/or vice versa. In some embodiments, the one or more induced currents may correspond to one or more signals generated by the transducer.

In some embodiments, the support structure may include two or more intertwined helically wound runners arranged in at least two complete revolutions per runner, referred to as a first runner and a second runner, and so on. The support structure may be arranged in a toroidal shape having a centroid. The centroid may be arranged at or near one or both of a subject and/or a body part of the subject, e.g. during treatment. As used herein, the terms therapy and treatment may be used interchangeably. One or more conductive wires may be wound spirally around the first runner, the second runner, and/or other runners. In some embodiments, conductive wires may be wound spirally around individual runners, e.g. in embodiments that include a first conductive wire and a second conductive wire. The leads of one or more conductive wires may be configured to be electrically coupled with one or more current sources to receive one or more currents through the conductive wires such that an electromagnetic field is created at or near the centroid that provides therapy to the subject.

In some embodiments, a conductive wire may be spirally wound around a runner to form a bifilar coil around the runner. In some embodiments, another conductive wire may be spirally wound around another runner to form another bifilar coil around the other runner. In some embodiments, the two leads of a first conductive wire (also referred to as first wire) are configured to be electrically coupled to a first current source to receive a first current. In some embodiments, the two leads of a second conductive wire (also referred to as second wire) may be configured to be electrically coupled to the same current source, or to a different current source, to receive a second current. The first current and/or second current may generate an electromagnetic field.

In some embodiments, the system may include one or more resistive elements. The one or more resistive elements may be coupled electrically to one or both of the first wire and/or the second wire such that a nominal impedance of the first wire, the second wire, and the one or more resistive elements has a predetermined value that substantially matches an impedance of one or more current sources.

One aspect of the invention relates to a method for providing therapy to a subject and/or for promoting health effects in a subject. The method may include arranging a support structure at or near one or both of the subject and/or a body part of the subject, inducing one or more currents that generate an electromagnetic field at or near one or both of the subject and/or the body part of the subject, obtaining (digital) information (e.g. from a digital audio file), processing the obtained information, generating a processed signal based on the obtained information, and producing sound signals based on the processed signal. The induced alternating currents may be controlled by and/or based on the produced sound signals. The support structure may include any of the features, functionality, and/or components as attributed to any support structures described elsewhere within this disclosure. The induced current may correspond to and/or be based on electronic streams and/or files, and/or on sensor-generated output signals and/or information derived from sensor-generated output signals.

These and other objects, features, and characteristics of the present disclosure, as well as the methods of operation and functions of the related components of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the any limits. As used in the specification and in the claims, the singular form of "a", "an", and "the" include plural referents unless the context clearly dictates otherwise.

DETAILED DESCRIPTION

Figure 1:
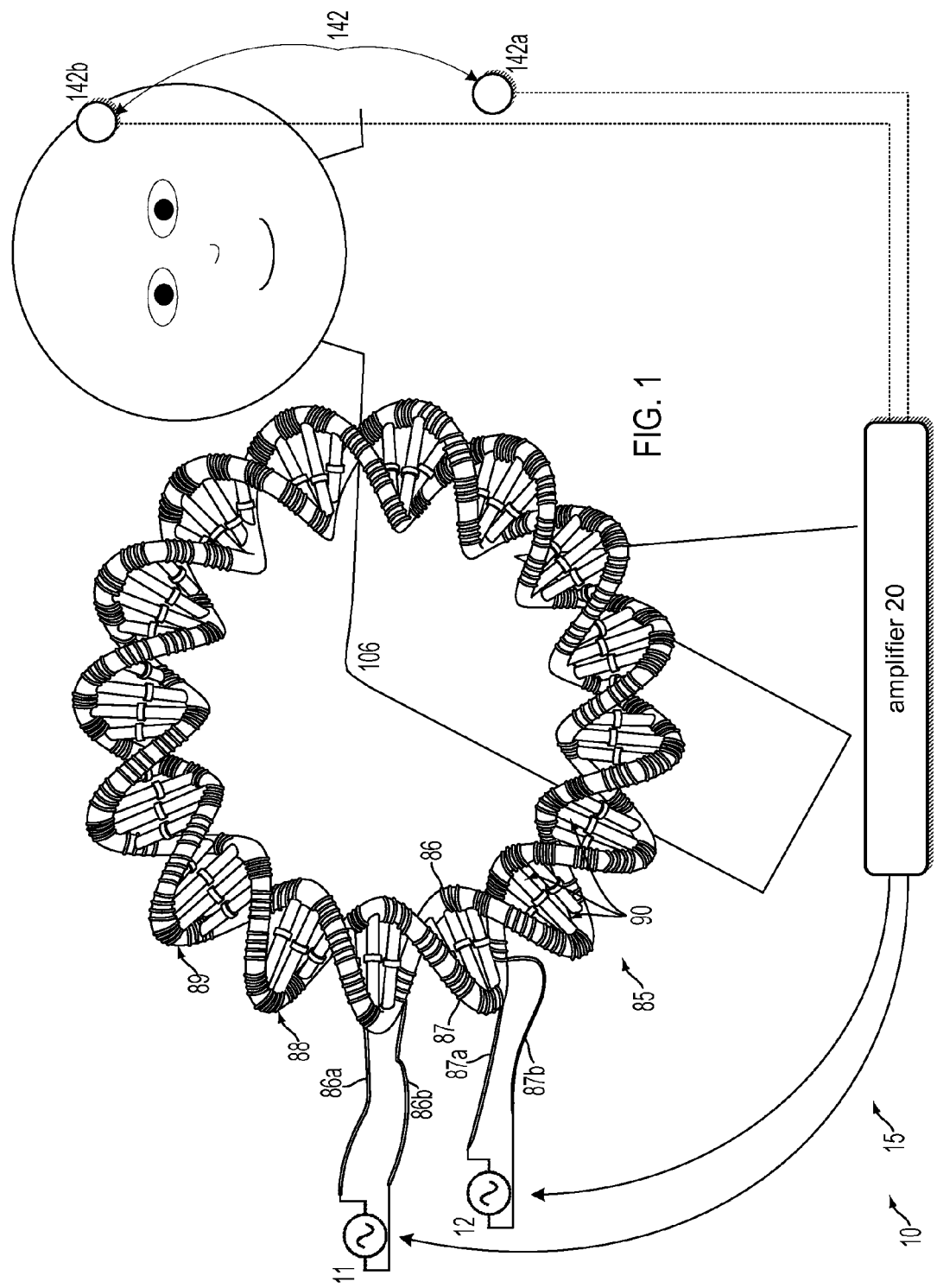
FIG. 1 schematically illustrates a system for providing therapy to a subject undergoing stem cell treatment, according to one or more embodiments.

FIG. 1 illustrates a system 10 for providing therapy to treat a subject 106 and/or for promoting health effects in subject 106, according to one or more embodiments. The therapy and/or health effects may include, but are not limited to, one or more of pain relief, relief of discomfort, reduction of inflammation, reduction of the level of free radicals, reduction of oxidative stress, improved range of motion, tissue repair, bone growth/repair, regenerative effects, improved circulation, improved micro-circulation, increased motility rate (of stem cells), accelerated healing, and/or other types of therapy and/or health effects on living organisms. The therapy and/or health effects may be used for various medical conditions and/or treatments, including but not limited to medical applications using stem cell technology. For example, the therapy may be used after stem cell transplantation. In some embodiments, the therapy may be used in vitro, e.g. prior to transplantation. The therapy and/or health effects may be used in conjunction with various medical treatments, techniques, and/or technologies. As used herein, the term "regenerative effects" may be used interchangeably with the term "regenerative medicine."

By way of non-limiting example, regenerative medicine may be interpreted to include the creation of living, functional tissue to repair and/or replace lost tissue and/or organ function. For example, tissue and/or organ function may be lost due to one or more of age, disease, damage, congenital defects, and/or other causes. In some embodiments, tissue and/or organs may be grown in a laboratory and subsequently implanted into patients.

A common application of stem cell technology may include stem cell transplantation or injection. However, stem cell transplantation may encounter a variety of issues, including but not limited to stem cells dying after transplantation, failing to take or graft to a site, harming a site, and/or other known and unknown causes of encountered issues. By virtue of the technology described in this disclosure, stem cell transplantation may be improved (before and/or after transplantation) through, by way of non-limiting example, reduction of inflammation, reduction of oxidative stress, increase of ATP available for newly transplanted stem cells, increase of motility rate for newly transplanted stem cells, and/or through other improvements. Alternatively, and/or simultaneously, fewer stem cells may be needed for a given procedure, the likelihood of a successful transplantation may be increased, a patient's discomfort may be reduced, the duration of treatment may be reduced, and/or other improvements may be enabled by virtue of the technology described in this disclosure. For example, by virtue of the technology described in this disclosure, the time required to proliferate a stem cell colony may be reduced, harvesting times may be reduced, and costs associated with proliferation and/or harvesting may be reduced.

Figure 2:
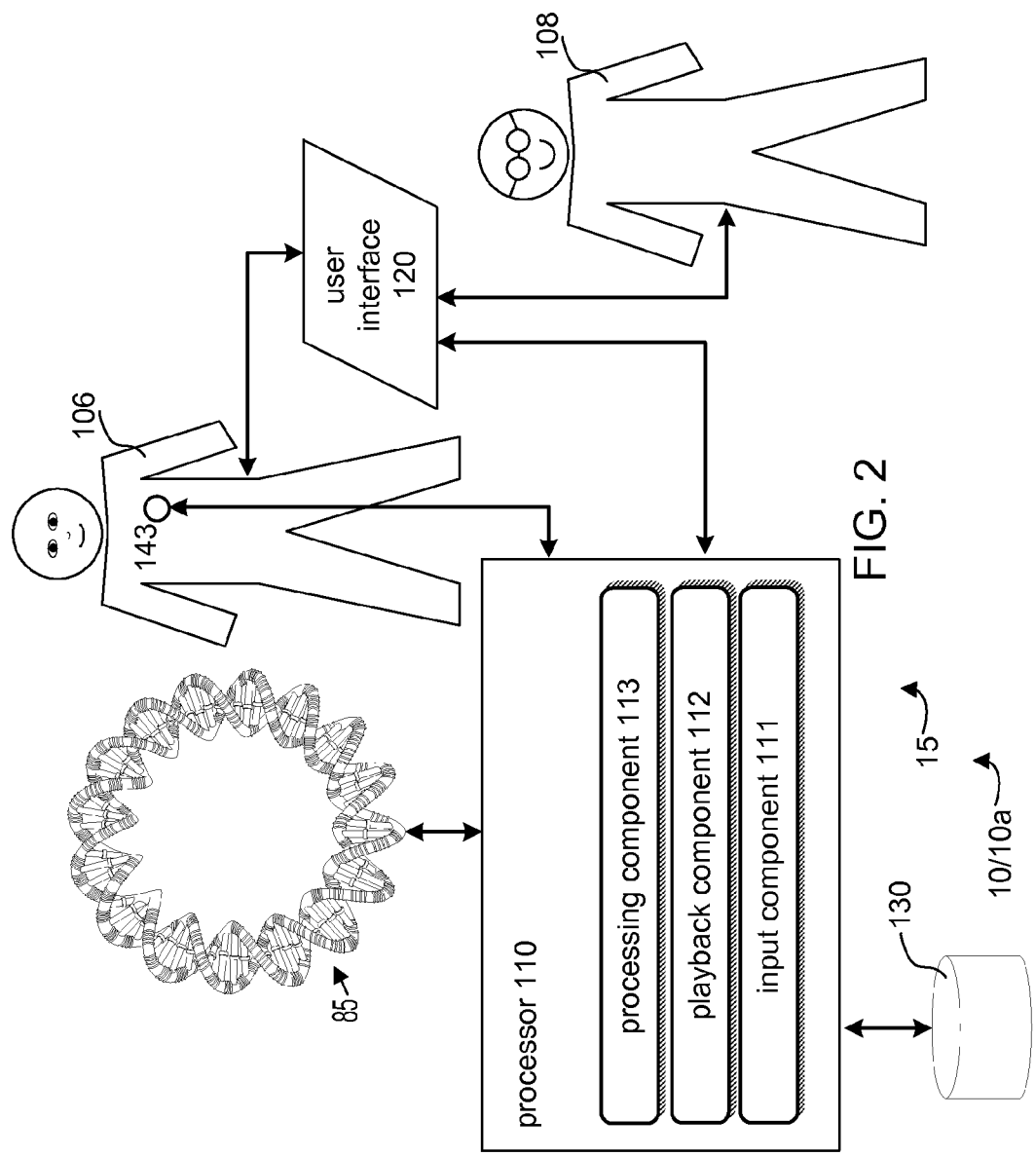
FIG. 2 schematically illustrates a system for providing therapy to a subject undergoing stem cell treatment, according to one or more embodiments.

System 10 may operate on organs, tendons, ligaments, bones, and/or other parts of a body. System 10 may include one or more of a field generator 15, one or more sensors 142 (e.g. a sensor 142a and/or a sensor 142b), one or more current sources (e.g. a current source 11 and/or a current source 12), an amplifier 20, and/or other components. Referring to FIG. 2, in some embodiments, system 10 may further include one or more of a transducer 143, one or more processors 110, a user interface 120, electronic storage 130, an input component 111, a playback component 112, a processing component 113, and/or other components. Features depicted in the figures and described in this disclosure may be combined in some embodiments.

Referring to FIG. 1, in some embodiments, field generator 15 may include one or more of a support structure 85, a first wire 86, and/or other components. The depiction of the size of subject 106 relative to the size of support structure 85 is not meant to be limiting.

Support structure 85 of system 10 in FIG. 1 as depicted includes two intertwined helically wound runners—runner 88 and runner 89—sharing the same (circular) axis, coupled by struts 90 and having one or more conductive wires spirally wound around one or both runners. In other words, runner 88 and runner 89 of support structure 85 form cores around which wire 86 and wire 87 are spirally wound, respectively. As depicted in FIG. 1, support structure 85 includes two wires: wire 86 and wire 87. In some embodiments, system 10 may include one runner, three runners, and/or another number of runners. Other support structures that substantially allow wires to be wound in a similar way as wire 86 and wire 87 (e.g. such that the wires form intertwined helical shapes and individual wires include a first and second helical shape that are nested hierarchically as depicted in FIG. 1) are considered within the scope of this disclosure. For example, in some embodiments, system 10 may include a support structure that does not include nor require struts that are similar to struts 90.

Runner 88 and runner 89 of support structure 85 and system 10 in FIG. 1 are arranged in the shape of a three-dimensional curve similar to or substantially the same as a helix, bend, twisted, and/or shaped with its ends arranged together. It is noted that the shape of support structure 85 resembles the general shape of DNA. The shape of the cross-section of a runner may include one or more of a circle, an oval, a square, a triangle, a rectangle, an angular shape, a polygon, and/or other shapes. The width and height of the cross-section of a runner may be limited for practical purposes. For example, for the purposes described herein, in some embodiments, it may be preferred to arrange support structure 85 such that there is available space within the periphery of support structure 85, as shown, e.g., in FIG. 1. As depicted in FIG. 1, the shape of the cross-section of runner 88 and runner 89 may be a circle. Note that embodiments of this disclosure are not intended to be limited by any of the given examples.

Runner 88, runner 89 and/or struts 90 of system 10 in FIG. 1 may be manufactured from one or more of plastic, plastic plated with metals including copper, nickel, iron, soft iron, nickel alloys, and/or other metals and alloys, and/or other materials. In some embodiments, runner 88, runner 89 and struts 90 are manufactured from non-conductive material. Runner 88, runner 89, and struts 90 may be manufactured from different materials. Runner 88, runner 89, and struts 90 may be manufactured through integral construction or formed separately prior to being assembled. The preceding statement is not intended to limit the (process of) manufacture of bodies similar to or substantially the same as support structure 85 in any way.

Referring to FIG. 1, wire 86 and wire 87, as any wire listed in any figure included in this description, may be insulated, uninsulated, or partially insulated and partially uninsulated.

The shape of support structure 85 of system 10 in FIG. 1 may be generally toroidal. In some embodiments, support structure 85 may be arranged in any planar shape, including circular, polygonal, and/or other shapes. Alternatively, and/or simultaneously, a support structure such as support structure 85 may be arranged in a three-dimensional curve (a.k.a. space curve). Runner 88 and runner 89 of support structure 85 may form bodies and/or cores around which wire 86 and wire 87 are spirally wound, respectively. As such, wire 86 and wire 87 may be arranged in a helical shape having axes that coincide with runner 88 and runner 89, respectively. As shown in FIG. 1, wire 86 and 87 may be wound such that they go around any of struts 90 of support structure 85 and/or around any points of engagement between one of struts 90 and one of runners 88 and 89. The number of wire turns per complete revolution of a runner and/or the number of wire turns between adjacent struts may be characteristic measurements/features of support structure 85. In FIG. 1, wire 86 and wire 87 are arranged to make approximately three to five turns between adjacent struts associated with runner 88 and runner 89, respectively, and/or some other number of turns. The depiction of FIG. 1 is intended to be exemplary, and in no way limiting.

Wire 86 may include two leads —86a and lead 86b. Wire 87 may include two leads—lead 87a and lead 87b. In system 10, support structure 85 is electrically coupled with one or more power sources and/or current sources, such as, e.g., current source 11 and/or current source 12, arranged such that electrical coupling with one or both of wire 86 and wire 87 may be established, e.g. through coupling of current source 11 with lead 86a and 86b of wire 86 and through coupling of current source 12 with lead 87a and 87b of wire 87. The current supplied to wire 86 may be a direct current or an alternating current. The current supplied to wire 87 may be a direct current or an alternating current. The currents supplied to wire 86 and wire 87 may flow in the same direction or the opposite direction. In some embodiments, the leads of wire 86 and wire 87 may be electrically coupled with the same current source.

For alternating currents, operating frequencies ranging from 0 Hz to 100 GHz are contemplated. Operating currents ranging from 1 pA to 10 A are contemplated. Operating voltages ranging from 1 mV to 20 kV are contemplated. In some embodiments, a root mean square voltage of less than about 1.6 V is supplied to wire 86 and/or wire 87. In some embodiments, a root mean square voltage of greater than about 0.25 V is supplied to wire 86 and/or wire 87. In a preferred embodiment, the frequency of the alternating current supplied to wire 86 and/or wire 87 is between 0 Hz and 20 kHz, and/or in the audible range. In some embodiments, the current is less than about 1 pA, 1 nA, 1 mA, 100 mA, 250 mA, 500 mA, and/or other amounts of current. The operating frequencies for wire 86 and wire 87 may be the same or different. Other electrical operating characteristics of current supplied to wire 86 and wire 87, such as phase, may be the same or different. System 10 may be used to exploit the electromagnetic field that is created in and/or around support structure 85 when electrical power is supplied to one or more wires of support structure 85. The electromagnetic field provides therapy to subject 106 and/or promotes health effects in a subject.

For the purposes of this description, the electromagnetic field may be an electromagnetic field of at least a predetermined threshold level of tesla. The predetermined threshold may be 1 pT, 1 nT, 1 mT, 10 mT, 100 mT, and/or another threshold. In some embodiments, the electromagnetic field may have a strength ranging between about 0.1 milligauss and about 100 milligauss, between about 1 milligauss and about 500 milligauss, and/or other ranges. The strength of the electromagnetic field may be measured at a predetermined distance from field generator 15 and/or support structure 85. The predetermined distance for such measurements may be about 1 inch, about 1 foot, about 3 feet, about 6 feet, and/or another distance.

Some embodiments of an electrical system including a support structure similar to or substantially the same as support structure 85 in FIG. 1, thus including wire 86 and wire 87, may be configured to have a current in wire 86 flowing in the opposite direction as the current flowing in wire 87. In some embodiments the current supplied to one wire may be a direct current, whereas the current supplied to another wire may be an alternating current. By way of non-limiting example, additional structures for a support structure and/or electrical systems using a support structure (which may be referred to as a "body") may be described in U.S. patent application Ser. No. 13/457,347, filed Apr. 26, 2012, and titled "System Configuration Using A Double Helix Conductor," as well as U.S. patent application Ser. No. 13/213,604, entitled "Double Helix Conductor," and filed Aug. 19, 2011, which are hereby incorporated into this disclosure by reference in its entirety. These patent applications may also be referred to as "the '347 application" and "the '604 application" herein. By way of non-limiting example, additional health applications, as well as structures for a support structure and/or electrical systems using a support structure (referred to as "body") may be described in U.S. patent application Ser. No. 13/458,716, filed Apr. 27, 2012, and titled "Health Applications of a Double Helix Conductor," as well as U.S. patent application Ser. No. 14/194,412, entitled "HEALTH APPLICATIONS FOR USING BIO-FEEDBACK TO CONTROL AN ELECTROMAGNETIC FIELD," and filed Feb. 28, 2014, which are hereby incorporated into this disclosure by reference in its entirety. These patent applications may also be referred to as "the '716 application" and "the '412 application" herein.

Some embodiments of an electrical system including a support structure similar to or substantially the same as support structure 85 may be configured to include one or more conductive wires that are wound to form a bifilar coil around one or more runners. In some embodiments, the windings may be one or more of caduceus windings, Ayrton-Perry winding, trifilar windings, windings of braided wires, and/or other types of windings. By way of non-limiting example, additional windings may be described in the '347 application and additional details of a support structure (referred to as "body") may be described in the '604 application.

In some embodiments, system 10 may include multiple support structures similar to or substantially the same as support structure 85. Currents for these multiple support structures may be supplied by one or more power sources and/or current sources.

In some embodiments, support structure 85 may be configured such that the dimensions of the available space within the periphery of support structure 85 and/or the passage formed through the centroid of the shape of support structure 85 are predetermined dimensions. In some embodiments, a predetermined dimension may include a diameter of about 1 inch, about 1 foot, about 2 feet, about 4 feet, about 6 feet, and/or another suitable dimension. Suitable dimensions may depend on average sizes of human fingers, wrists, elbows, arms, ankles, knees, legs, shoulders, (lower) backs, torsos, bodies, and/or other body parts, as may be used as an area to receive treatment and/or therapy. By way of non-limiting example, additional information regarding (full-body) applications of electrical system similar to the systems described herein may be described in the '716 application.

In some embodiments, lead 86*a* and 86*b* of wire 86 and lead 87*a* and 87*b* of wire 87 are electrically coupled in the same circuit. This circuit may include, for example, one or more resistive components, such as resistors, that are arranged such that the circuit has a nominal impedance of a predetermined value, such as, e.g., 4 ohms, 8 ohms, 16 ohms, 32 ohms, 100 ohms, 600 ohms, and/or another predetermined value. In some embodiments, the predetermined value may be chosen to match the impedance of standard consumer electronics components and/or systems, including for example audio consumer electronics. These examples are not intended to be limiting in any way. By way of non-limiting example, additional information regarding resistive elements and/or impedance matching may be described in the '347 application.

Referring to FIG. 1, the one or more sensors 142 are configured to generate output signals conveying electrophysiological information and/or measurements related to one or more organs and/or body parts of subject 106. In some embodiments, the one or more sensors 142 may be non-invasive. For example, the one or more sensors 142 may be configured to not penetrate the skin of subject 106, but rather to be placed against or near the skin of subject 106. The one or more sensors 142 may include, as depicted in FIG. 1, a (first) sensor 142*a* and a (second) sensor 142*b*. The placement, type, and number of sensors 142 is not intended to be limited by the depictions in any figures. In some embodiments, system 10 may include 1 sensor, 3 sensors, and/or another number of sensors. As depicted in FIG. 1, sensor 142*a* may be positioned at or near the heart of subject 106 (e.g. on the skin of the chest of subject 106). As depicted in FIG. 1, sensor 142*b* may be positioned and/or located at or near the brain of subject 106 (e.g. on or near the head or skull of subject 106).

In some embodiments, the one or more sensors 142 may include an audio sensor, a microphone, a stethoscope, an electronic stethoscope, a pressure sensor, a motion sensor, a proximity sensor, an electromagnetic sensor, an electrode, a temperature sensor, a current sensor, an optical sensor, an electro-optical sensor, a heart monitor, an electro interstitial scanning (EIS) sensor and/or device, a bioelectrical impedance sensor and/or device, a BioPulsar©, and/or other sensors, devices, and/or combinations thereof. In some embodiments, the one or more sensors 142 may be configured to measure electrical and/or electrophysiological signals at or near subject 106, and/or emitted by subject 106. The one or more sensors 142 may be configured to convey sounds, currents, voltages, electromagnetic fields caused and/or emitted naturally by subject 106. Measured signals may pertain to respiratory characteristics and/or parameters of subject 106, cardiac/coronary characteristics and/or parameters of subject 106, hemodynamic characteristics and/or parameters of subject 106, neural characteristics and/or parameters of subject 106, brain-related characteristics and/or parameters of subject 106, and/or other characteristics and/or parameters. In some embodiments, measured signals may pertain and/or correspond to electroencephalography (EEG) measurements, magnetoencephalography (MEG) measurements, electrocardiography (EKG or ECG) measurements, heart rate variability (HRV) measurements, acoustic cardiograph (ACG) measurements, and/or other measurements. As used herein, correspondence of a generated output signal to, for example, an EEG signal refers to a generated output signal that includes similar information as a sensor-generated signal used for a standard EEG measurement. In some embodiments, measurements may be related to heart function, for example pertaining to the P wave, the PR interval, the PR segment, the QRS complex, the ST segment, the T wave, the ST interval, the QT interval, the U wave, the J wave, one or more heart valves, and/or other functions/periods/amplitudes that may be measured using EKG, derivatives thereof, and/or combinations thereof. Alternatively, and/or simultaneously, measurements related to heart functions may pertain to levels, functions, periods, and/or amplitudes that may be measured by techniques other than EKG.

In some embodiments, the one or more sensors 142 may be configured to generate output signals in an ongoing manner, e.g. throughout the day or during a treatment session. This may include generating signals intermittently, periodically (e.g. at a sampling rate), continuously, continually, at varying intervals, and/or in other ways that are ongoing during at least a portion of period of a day, week, month, treatment, or other duration. The sampling rate may be about 0.001 second, 0.01 second, 0.1 second, 1 second, about 10 seconds, about 1 minute, and/or other sampling rates. It is noted that multiple individual sensors may operate using different sampling rates, as appropriate for the particular output signals and/or (frequencies related to particular) parameters derived therefrom. For example, in some embodiments, the generated output signals may be considered as a vector of output signals, such that a vector includes multiple samples of information conveyed related to one or more types of electrophysiological information of subject 106. Different parameters may be related to different vectors. A particular parameter determined in an ongoing manner from a vector of output signals may be considered as a vector of that particular parameter.

Referring to FIG. 1, in some embodiments, system 10 may include amplifier 20. Amplifier 20 may be configured to amplify signals. Amplifier 20 may include an input and an output, such that amplifier 20 amplifies the signal presented on the input and provides the amplified signal to the output. The input signals for amplifier 20 may be electrically coupled to and/or based on sensor-generated output signals from the one or more sensors 142. In some embodiments, the input signals for amplifier 20 may include an acoustic signal. The output signals of amplifier 20 may be electrically coupled to and/or form the basis of the signals driving field generator 85. In some embodiments, output signals from amplifier 20 may be directly electrically coupled to the electrical leads of wire 86 and/or wire 87 without use of current source 11 or current source 12. In some embodiments, output signals from amplifier 20 may be used to control the operation of current source 11 and/or current source 12, which in turn may induce one or more electrical currents through wire 86 and/or wire 87. In some embodiments, the one or more induced alternating currents may be dynamically controlled such that one or more frequencies of one or more alternating currents correspond to one or more frequencies of the sensor-generated output signals.

By way of illustration, FIG. 2 schematically illustrates a system 10a for providing therapy to a subject and/or promoting health effects in a subject. System 10a may include similar or the same features as system 10 in FIG. 1. For example, support structure 85 of system 10a in FIG. 2 may be similar to or the same as support structure 85 of system 10 in FIG. 1, and so forth.

System 10a may include, in addition to any of the components, features, and functionality described in relation to system 10 (FIG. 1), one or more of processor(s) 110, user interface 120, electronic storage 130, transducer 143, one or more computer program components, and/or other components.

Transducer 143 may include one or more of a microphone, a stethoscope (analog and/or digital), and/or other devices and/or components. Transducer 143 may be configured to convert acoustic signals to one or more electrical signals.

Processor 110 of system 10a in FIG. 2 is configured to provide information processing capabilities in system 10a. As such, processor 110 includes one or more of a digital processor, an analog processor, a digital circuit designed to process information, a central processing unit, a graphics processing unit, an analog circuit designed to process information, and/or other mechanisms for electronically processing information. Although processor 110 is shown in FIG. 2 as a single entity, this is for illustrative purposes only. In some embodiments, processor 110 may include a plurality of processing units.

As is shown in FIG. 2, processor 110 is configured to execute one or more computer program components. The one or more computer program components may include one or more of input component 111, playback component 112, processing component 113, and/or other components. Processor 110 may be configured to execute components 111-113 by software; hardware; firmware; some combination of software, hardware, and/or firmware; and/or other mechanisms for configuring processing capabilities on processor 110.

It should be appreciated that although components 111-113 are illustrated in FIG. 2 as being co-located within a single processing unit, in embodiments in which processor 110 includes multiple processing units, one or more of components 111-113 may be located remotely from the other components. The description of the functionality provided by the different components 111-113 described herein is for illustrative purposes, and is not intended to be limiting, as any of components 111-113 may provide more or less functionality than is described. For example, one or more of components 111-113 may be eliminated, and some or all of its functionality may be incorporated, shared, integrated into, and/or otherwise provided by other ones of components 111-113. Note that processor 110 may be configured to execute one or more additional components that may perform some or all of the functionality attributed below to one of components 111-113.

Referring to FIG. 2, input component 111 may be configured to obtain information. In some embodiments, the information may be obtained based on sensor-generated output signals from one or more sensors 142 (shown in FIG. 1). In some embodiments, the information may be obtained based on an electrical signal from transducer 143. In some embodiments, the information may be obtained through a microphone or other acoustic-to-electric transducer and/or sensor. For example, input component 111 may be configured to obtain an electrical signal that represents the sound of the heartbeat of subject 106, and/or one or more sounds related to the mitral valve, the tricuspid valve, the aortic valve, and/or the pulmonary valve of subject 106.

In some embodiments, the information may be obtained from storage, e.g. from electronic storage. In some embodiments, the information may be obtained from a stream of information, e.g. streaming via the internet or via radio. Information obtained from storage or through streaming may include (digital) audio files in any format, including but not limited to MP3, WMA, WAV, AIFF, and/or other audio formats. Audio formats may be uncompressed, have lossless compression, and/or lossy compression. In some embodiments, the audio file may be pre-programmed, e.g. to include a sine wave or square wave between about 20 Hz and about 20 kHz, e.g. at 100 Hz.

In some embodiments, information may be obtained from traditional sound sources including phonographs, CD-players, DVD players, AM radio, FM radio, and/or other sound sources. Electronic storage may be local to system 10a and/or be accessible from a remote location through a network connection, such as e.g. the internet. In some embodiments, information obtained by input component 111 may be a combination of one or more of sensor-generated output signals (from one or more sensors 142), one or more electrical signals (from transducer 143), and/or information obtained from storage.

In some embodiments, information may be obtained from a combination of a sensor-generated or sensor-based signal and information obtained from storage or through streaming.

Referring to FIG. 2, processing component 113 may be configured to process the obtained information from input component 111. Processing component 113 may be configured to generate a processed signal based on the obtained information. For example, processing component 113 may convert, filter, modify, and/or otherwise transform information or signals from input component 111 to generate the processed signal. In some embodiments, the obtained signal may be a coronary or cardiac signal having a first range of frequencies. Processing component 113 may be configured to transform the first range of frequencies into a second range of frequencies, using signal processing techniques, such that the second range of frequencies may be suitable for acoustic reproduction of the processed signal. In some embodiments, the obtained signal may represent heart and/or brain activity, and have a first range of frequencies. Through filtering, conversion, transformation, and/or other signal processing techniques, the processed signal may have a second range of frequencies. The second range may be (designed to be) suitable for acoustic reproduction, e.g. by playback component 112.

Playback component 112 may be configured to produce sound signals based on the processing signal from processing component 113. Alternatively, and/or simultaneously, playback component 112 may be configured to produce sound signals based on the obtained information from input component 111. For example, playback component 112 may be configured to produce sound signals based on the obtained electrical signal that represents the sound of the heartbeat of subject 106. The produced sound signals, though possibly processed through processing component 113, may represent the sound of the heartbeat of subject 106. Other naturally occurring sounds, electromagnetic signals, and/or electrophysiological information produced or emitted by subject 106 are considered within the scope of this disclosure.

The sound signals produced by playback component 112 may be analog and/or digital signals. The sound signals produced by playback component 112 may be electric, optical, and/or using other media. The sound signals produced by playback component 112 may be accessible through one or more signal connectors, including but not limiting to line out connectors, tip-ring-sleeve (TRS) connectors, tip-ring-ring-sleeve (TRRS) connectors, TOSLINK connectors, S/PDIF connectors, FireWire™ connectors, HDMI connectors, DVI connectors, USB connectors, and/or other connectors capable of transferring an audio signal. The sound signals produced by playback component 112 may be electrically coupled to the leads of the one or more conductive wires of support structure 85 (depicted in FIG. 2) such that current through the one or more conductive wires of support structure 85 corresponds to the produced sound signals. For example, the induced currents may be dynamically controlled to correspond to the sound signals produced by playback component 112, to correspond to the processed signal generated by processing component 113, to correspond to information obtained by input component 111, and/or to correspond to output signals generated by one or more sensors 142 and/or transducer 143.

In some embodiments, the sound signals produced by playback component 112 may be amplified by amplifier 20 before being electrically coupled to the leads of the one or more conductive wires of support structure 85. In some preferred embodiments, amplifier 20 may be an audio amplifier ranging between 100 W and 400 W. Other types of amplifiers and/or amplifiers having a different power range are also contemplated.

In some embodiments, the sound signals produced by playback component 112 may be used to control one or more current sources, e.g. current source 11 and/or current source 12, which in turn induce alternating currents in field generator 15 as described elsewhere.

In some embodiments, system 10 may be configured such that the cross-section of the toroidal shape of field generator 15 is between about 3 inches and about 8 inches, and such that the diameter of the passage formed through support structure 85 is between about 1 foot and about 4 foot. In some embodiments, field generator 15 may be suspended between about 1 foot and about 3 foot from (e.g. above) subject 106 and/or, in particular, from the body part of subject 106 that is to be treated. For example, as treatment, field generator 15 may be suspended about 1 foot above the transplantation area. By way of example, and not limitation, a treatment may include multiple periods during which amplifier 20 is set to different percentages of output power. For example, during the first period of 5 minutes, amplifier 20 may be set to 25% of available power, during the second period of 5 minutes, amplifier 20 may be set to 50% of available power, during the third period of 5 minutes, amplifier 20 may be set to 75% of available power, and during the fourth period of between 5 and 15 minutes, amplifier 20 may be set to 100% of available power.

Figure 5:
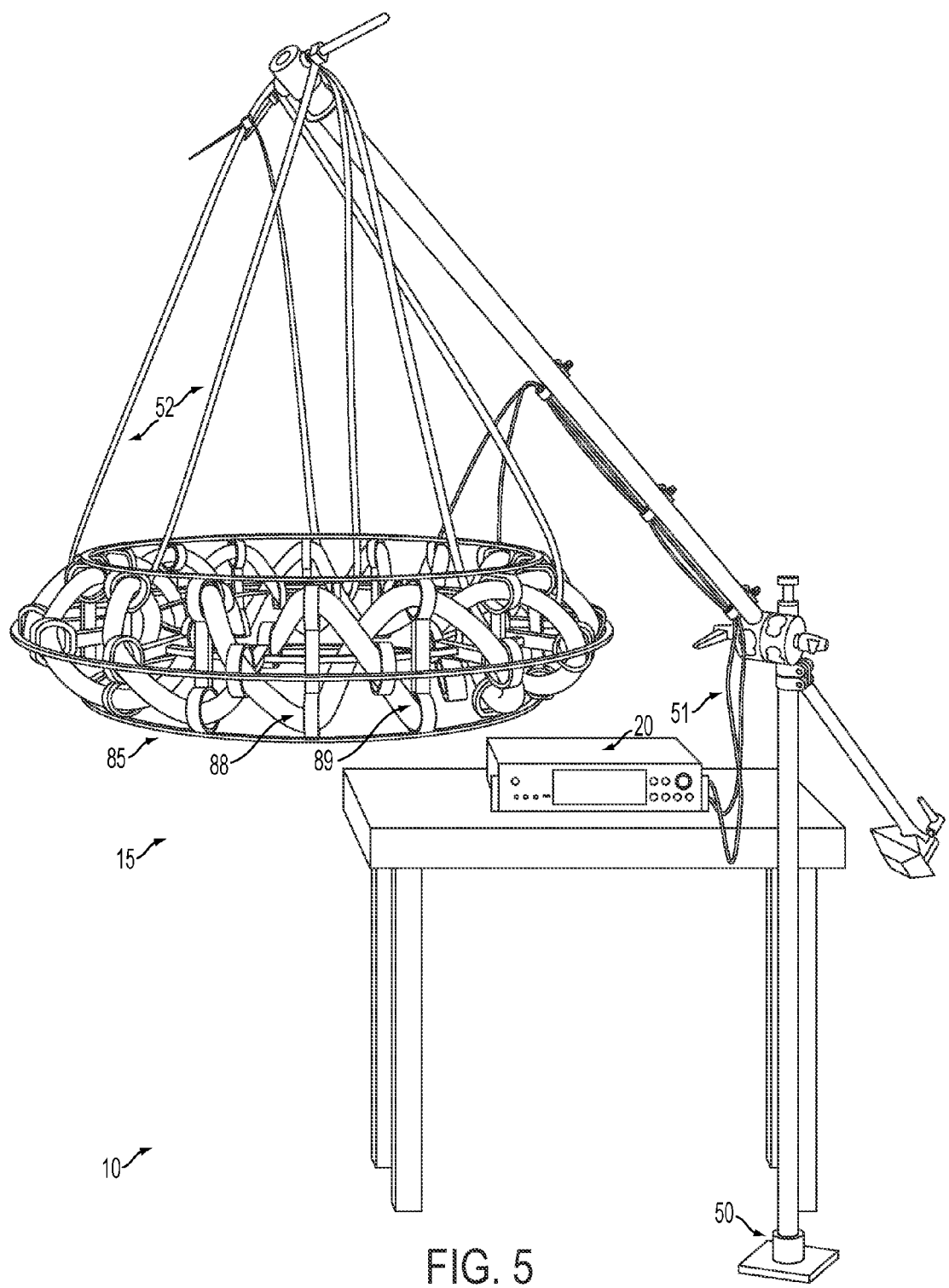
FIG. 5 illustrates a system for providing therapy to treat a neuropathic disorder of a subject, according to one or more embodiments.

By way of illustration, FIG. 5 illustrates an embodiment of system 10 for providing therapy to treat a neuropathic disorder of subject 106. FIG. 5 depicts field generator 15 including support structure 85 and two helically wound runners, runner 88 and runner 89. As depicted, runners 88 and 89 are spirally wound with twisted wires (not depicted) that are connected, via audio cables 51, to amplifier 20. Support structure 85 is suspended from a crane 50 using straps 52. A subject would lie down and/or be positioned 1 to 3 feet below field generator 15, for example on a massage table. Specifically, in some embodiments, field generator 15 may be positioned to be directly above a particular part of the patient's body, e.g. the injection site of stem cells.

Electronic storage 130 of system 10a in FIG. 2 comprises electronic storage media that electronically stores information. The electronic storage media of electronic storage 130 may include one or both of system storage that is provided integrally (i.e., substantially non-removable) with system 10a and/or removable storage that is connectable to system 10a via, for example, a port (e.g., a USB port, a Firewire port, etc.) or a drive (e.g., a disk drive, etc.). Electronic storage 130 may include one or more of optically readable storage media (e.g., optical disks, etc.), magnetically readable storage media (e.g., magnetic tape, magnetic hard drive, floppy drive, etc.), electrical charge-based storage media (e.g., EPROM, EEPROM, RAM, etc.), solid-state storage media (e.g., flash drive, etc.), and/or other electronically readable storage media. Electronic storage 130 may store software algorithms, information determined by processor 110, information received via user interface 120, and/or other information that enables system 10a to function properly. For example, electronic storage 130 may store sound information and/or electronic audio files (as discussed elsewhere herein), and/or other information. Electronic storage 130 may be a separate component within system 10a, or electronic storage 130 may be provided integrally with one or more other components of system 10a (e.g., processor 110).

User interface 120 of system 10a in FIG. 2 is configured to provide an interface between system 10a and a user (e.g., user 108, subject 106, a caregiver, a therapy decision-maker, etc.) through which the user can provide information to and receive information from system 10a. This enables data, results, and/or instructions and any other communicable items, collectively referred to as "information," to be communicated between the user and system 10a. An example of information that may be conveyed to user 108 is an indication of the volume and/or intensity of the sound signals produced by playback component 112. Examples of interface devices suitable for inclusion in user interface 120 include a keypad, buttons, switches, a keyboard, knobs, levers, a display screen, a touch screen, speakers, a microphone, an indicator light, an audible alarm, and a printer. Information may be provided to user 108 or subject 106 by user interface 120 in the form of auditory signals, visual signals, tactile signals, and/or other sensory signals.

It is to be understood that other communication techniques, either hard-wired or wireless, are also contemplated herein as user interface 120. For example, in one embodiment, user interface 120 may be integrated with a removable storage interface provided by electronic storage 130. In this example, information is loaded into system 10a from removable storage (e.g., a smart card, a flash drive, a removable disk, etc.) that enables the user(s) to customize system 10a. Other exemplary input devices and techniques adapted for use with system 10a as user interface 120 include, but are not limited to, an RS-232 port, RF link, an IR link, modem (telephone, cable, Ethernet, internet or other). In short, any technique for communicating information with system 10a is contemplated as user interface 120.

Figure 3:
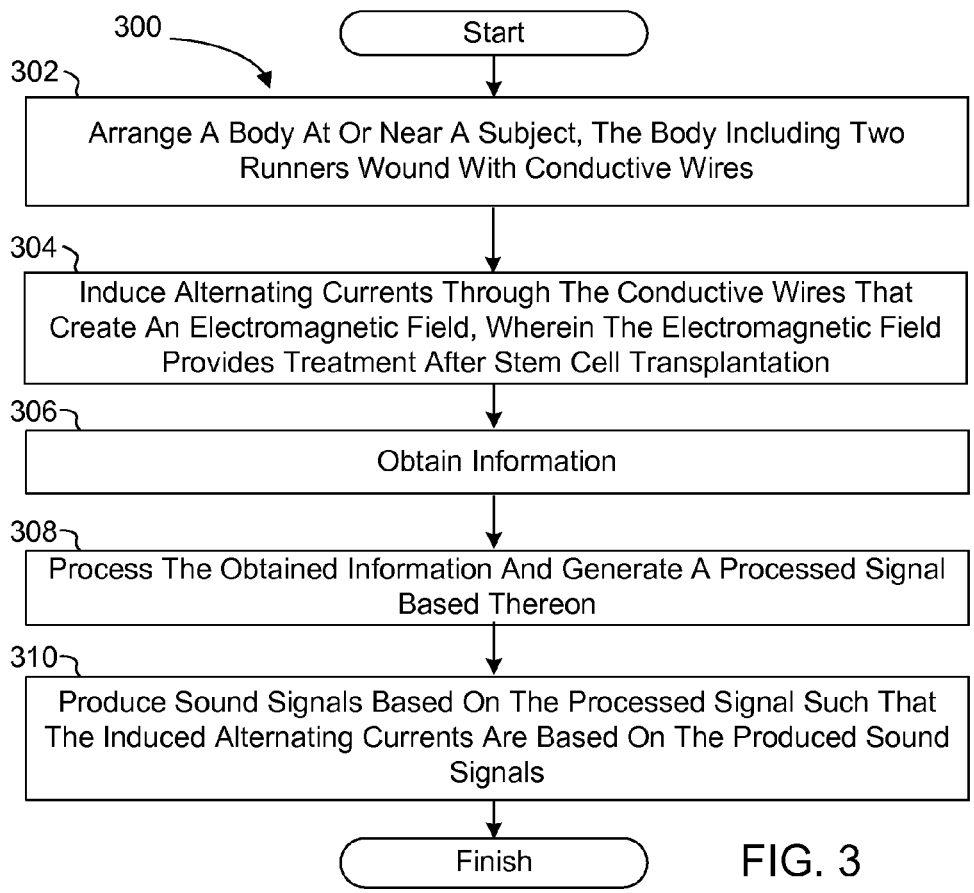
FIGS. 3 and 4 illustrate methods for providing therapy to a subject undergoing stem cell treatment, according to one or more embodiments.
Figure 4:
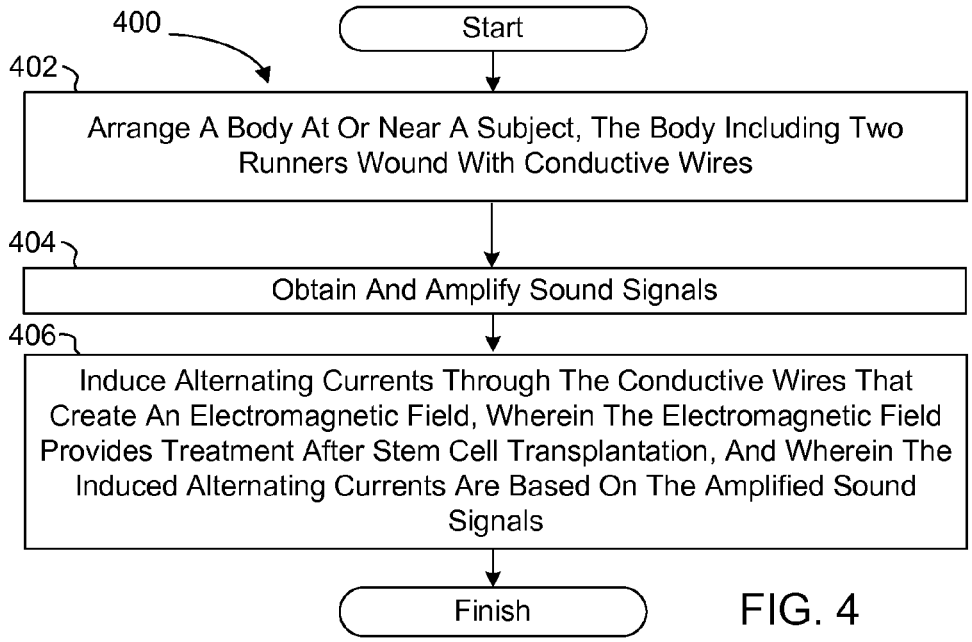

FIGS. 3 and 4 illustrate methods 300 and 400 for providing therapy to treat a subject by using electromagnetic fields applied to stem cells. The operations of methods 300-400 presented below are intended to be illustrative. In certain embodiments, methods 300-400 may be accomplished with one or more additional operations not described, and/or without one or more of the operations discussed. Additionally, the order in which the operations of methods 300-400 are illustrated in FIGS. 3 and 4 and described below is not intended to be limiting.

In certain embodiments, methods 300-400 may be implemented in one or more processing devices (e.g., a digital processor, an analog processor, a digital circuit designed to process information, an analog circuit designed to process information, and/or other mechanisms for electronically processing information). The one or more processing devices may include one or more devices executing some or all of the operations of methods 300-400 in response to instructions stored electronically on an electronic storage medium. The one or more processing devices may include one or more devices configured through hardware, firmware, and/or software to be specifically designed for execution of one or more of the operations of methods 300-400.

Regarding method 300 and FIG. 3, at an operation 302, a support structure is arranged at or near the subject. The support structure includes a first runner and a second runner. The first runner and second runner are helically intertwined. The support structure is arranged in a toroidal shape having a centroid. A first wire is wound around the first runner and a second wire is wound around the second runner. The first wire and second wire are conductive. In some embodiments, operation 302 is performed by a support structure the same as or similar to support structure 85 (shown in FIG. 1 and described herein).

At an operation 304, alternating currents are induced through the first wire and the second wire such that the alternating currents create an electromagnetic field at or near the centroid. The electromagnetic field provides treatment before and/or after stem cell transplantation. In some embodiments, operation 304 is performed by a current source the same as or similar to current source 11 and/or current source 12 (shown in FIG. 1 and described herein).

At an operation 306, information is obtained by a physical processor. The information may be obtained from one or more digital audio files, or may be based on electrophysiological information of a subject, e.g. through a measurement. The obtained information may be static and/or dynamic. In some embodiments, operation 306 is performed by a processor the same as or similar to processor 110 (shown in FIG. 2 and described herein).

At an operation 308, the obtained information is processed and a processed signal is generated based on the obtained information. In some embodiments, operation 308 is performed by an input component and/or a processing component the same as or similar to input component 111 and/or processing component 113 (shown in FIG. 2 and described herein).

At an operation 310, sound signals are produced based on the processed signal. The induced alternating currents may be controlled by and/or based on the produced sound signals. In some embodiments, operation 310 is performed by a playback component the same as or similar to playback component 112 (shown in FIG. 2 and described herein).

Regarding method 400 and FIG. 4, at an operation 402, a support structure is arranged at or near the subject. The support structure includes a first runner and a second runner. The first runner and second runner are helically intertwined. The support structure is arranged in a toroidal shape having a centroid. A first wire is wound around the first runner and a second wire is wound around the second runner. The first wire and second wire are conductive. In some embodiments, operation 402 is performed by a support structure the same as or similar to support structure 85 (shown in FIG. 1 and described herein).

At an operation 404, sound signals are obtained and amplified. In some embodiments, operation 404 is performed by an amplifier the same as or similar to amplifier 20 (shown in FIG. 1 and described herein).

At an operation 406, alternating currents are induced through the first wire and the second wire such that the alternating currents create an electromagnetic field at or near the centroid. The electromagnetic field provides treatment before and/or after stem cell transplantation. The induced alternating currents are based on the amplified sound signals. In some embodiments, operation 406 is performed by a current source the same as or similar to current source 11 and/or current source 12 (shown in FIG. 1 and described herein).

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment. For example, in some embodiments, system 10 may include amplifier 20 (shown in FIG. 1), as well as one or more computer program components 111-113 (shown in FIG. 2).

What is claimed is:

1. A method for providing therapy to a subject by using electromagnetic fields applied to stem cells, the method comprising:
arranging a support structure and the subject with respect to each other so that the subject is at or near the support structure, wherein the support structure includes a first runner and a second runner, wherein the first runner and second runner are helically intertwined, wherein the support structure is arranged in a toroidal shape having a centroid, wherein a first wire is wound around the first runner and a second wire is wound around the second runner, wherein the first wire and second wire are conductive;
inducing alternating currents through the first wire and the second wire such that the alternating currents create an electromagnetic field at or near the centroid;
providing treatment through the electromagnetic field before and/or after stem cell transplantation;
obtaining, by a physical processor, information;
processing the obtained information and generating a processed signal based on the obtained information; and
producing sound signals based on the processed signal, wherein the induced alternating currents are based on the produced sound signals.

2. The method of claim 1, wherein the obtained information includes one or more digital audio files.

3. The method of claim 1, further comprising:
generating output signals conveying electrophysiological information related to one or more body parts of the subject,
wherein the obtained information includes the generated output signals, and wherein inducing the alternating currents includes dynamically controlling the alternating currents to correspond to the generated output signals such that one or more frequencies of the alternating currents correspond to one or more frequencies of the generated output signals.

4. The method of claim 1, wherein the produced sound signals include frequencies that range predominantly between 20 Hz and 20 kHz.

5. The method of claim 1, wherein the first runner is arranged in a first helical shape, wherein the second runner is arranged in a second helical shape.

6. The method of claim 5, wherein the first wire is arranged in a third helical shape formed around the first helical shape of the first runner, and wherein the second wire is arranged in a fourth helical shape formed around the second helical shape of the second runner.

7. The method of claim 1, further comprising:
amplifying the sound signals,
wherein the induced alternating currents are based on the amplified sound signals.

8. The method of claim 3, wherein the one or more body parts include heart and/or brain.

9. The method of claim 3, wherein the one or more body parts include liver, pancreas, and/or kidney.

10. The method of claim 3, wherein the generated output signals correspond to one or more of electroencephalography (EEG) signals, electrocardiography (EKG) signals, magnetoencephalography (MEG) signals, and/or acoustic cardiograph (ACG) signals.

11. A method for providing therapy to a subject by using electromagnetic fields applied to stem cells, the method comprising:
arranging a support structure and the subject with respect to each other so that the subject is at or near the support structure, wherein the support structure includes a first runner and a second runner, wherein the first runner and second runner are helically intertwined, wherein the support structure is arranged in a toroidal shape having a centroid, wherein a first wire is wound around the first runner and a second wire is wound around the second runner, wherein the first wire and second wire are conductive;
obtaining and amplifying sound signals;
inducing alternating currents through the first wire and the second wire such that the alternating currents create an electromagnetic field at or near the centroid; and
providing treatment through the electromagnetic field before and/or after stem cell transplantation, and wherein the induced alternating currents are based on the amplified sound signals.

12. The method of claim 11, wherein the obtained sound signals are included in one or more digital audio files.

13. The method of claim 11, further comprising:
generating output signals conveying electrophysiological information related to one or more body parts of the subject,
wherein the obtained sound signals include the generated output signals, and wherein inducing the alternating currents includes dynamically controlling the alternating currents to correspond to the generated output signals such that one or more frequencies of the alternating currents correspond to one or more frequencies of the generated output signals.

14. The method of claim 11, wherein the sound signals include frequencies that range predominantly between 20 Hz and 20 kHz.

15. The method of claim 11, wherein the first runner is arranged in a first helical shape, wherein the second runner is arranged in a second helical shape.

16. The method of claim 15, wherein the first wire is arranged in a third helical shape formed around the first helical shape of the first runner, and wherein the second wire is arranged in a fourth helical shape formed around the second helical shape of the second runner.

17. The method of claim 13, wherein the one or more body parts include heart and/or brain.

18. The method of claim 13, wherein the one or more body parts include liver, pancreas, and/or kidney.

19. The method of claim 13, wherein the generated output signals correspond to one or more of electroencephalography (EEG) signals, electrocardiography (EKG) signals, magneto-encephalography (MEG) signals, and/or acoustic cardiograph (ACG) signals.

* * * * *